United States Patent [19]
Lee et al.

[11] Patent Number: 5,317,088
[45] Date of Patent: May 31, 1994

[54] C-TERMINAL CONGLUTININ FRAGMENTS COUPLED TO SOLID SUPPORT

[75] Inventors: Young M. Lee, Carmichael; Kevin R. Leiby; Thomas B. Okarma, Palo Alto, all of Calif.

[73] Assignee: Applied Immune Sciences, Inc., Santa Clara, Calif.

[21] Appl. No.: 921,296

[22] Filed: Jul. 28, 1992

Related U.S. Application Data

[63] Continuation of Ser. No. 433,546, Nov. 8, 1989, abandoned.

[51] Int. Cl.$^5$ .................. A61K 37/02; C07K 3/00; C07K 5/00; C07K 17/00
[52] U.S. Cl. .................. 530/350; 530/322; 530/324; 530/333; 530/334; 530/344; 530/345; 530/402; 530/403; 530/412; 530/413; 435/240.1; 435/240.2; 536/127
[58] Field of Search ............ 530/333, 332, 334, 324, 530/325, 326, 327, 328, 350, 356, 395, 396, 380, 344, 345, 402, 403, 412, 413; 536/127; 435/240.2, 240.1

[56] References Cited

U.S. PATENT DOCUMENTS 4,906,734 3/1990 Jensenius .................. 530/395

OTHER PUBLICATIONS

Oka et al. (1987) J. Biochem. 101, 135–144.
Davis et al. (1984) Biochemistry 23, 2139–2144.
Young et al. (Mar. 13, 1987) Biochemical and Biophysical Research Communications vol. 143, #2, pp. 645–651.
Kawasaki et al. (1985) J. Biochem. 98 pp. 1309–1320.
Strang et al. (1986) Biochemical Journal vol. 234, pp. 381–389.

Primary Examiner—Robert J. Hill, Jr.
Assistant Examiner—Gian P. Wang
Attorney, Agent, or Firm—Morrison & Foerster

[57] ABSTRACT

Peptide fragments of conglutinin are provided for use in binding to complementary ligands. Particularly, an N-proximal region is provided having a hypervariable region with a collagen type structure for binding to complementary molecules, and a C-proximal region which provides for lectin binding activity.

3 Claims, 3 Drawing Sheets

FIG. 1A

1. CLEAVAGE AT Asn-Gly
2. CLEAVAGE AT Lys
3. CLEAVAGE WITH COLLAGENASE
4. CLEAVAGE OF CL1 WITH TRYPSIN

C-TERMINAL CONGLUTININ FRAGMENTS COUPLED TO SOLID SUPPORT

This application is a continuation of application Ser. No. 07/433,546 filed 8 Nov. 1989, now abandoned.

INTRODUCTION

1. Technical Field

The field of this invention is the preparation of conglutinin cross-reactive materials by recombinant DNA technology.

2. Background

Conglutinin is a bovine serum protein with structural similarity to several extracellular glycoprotein receptors. The intact molecule exhibits multimeric structure in which disulfide-linked trimers are associated to form the tetravalent macromolecule. Conglutinin has been described as a calcium ion dependent lectin which can bind immune complexes and which may play a role in the ruminant immune response. The exact physiological function of the protein, however, has not been clearly defined. Previous structural studies show conglutinin to be a collagen-like molecule based upon very limited amino terminal sequence data.

There is substantial interest in developing compounds which specifically bind to sugars, where the sugars may be associated with specific molecules or families of molecules. S. aureus protein A has found extensive use in the isolation of immune complexes. Other lectins can also find use in isolating physiologically active molecules having a particular polysaccharide or monosaccharide group. These compositions may find use in the isolation and purification of molecules of interest. There is, therefore, substantial interest in isolating various lectins, defining those regions associated with binding, and developing techniques for their commercial production.

3. Relevant Literature

Descriptions concerning the physical and chemical properties of conglutinin may be found in Strang et al., *Biochemistry J.* 234:381–389 (1986); Lachmann and Muller-Eberhard, *J. Immunol.* 100:691–698 (1968); Linacott et al., ibid 121:658–664 (1978); Ingram, *Immunology* 2:322–333 (1959); Ingram, ibid 2:334–345 (1959); and Davis and Lachmann, *Biochemistry*, 23:2139–2144, (1984).

SUMMARY OF THE INVENTION

Functional fragments of conglutinin are provided, where the fragments provide for collagen-like activity or lectin-like activity. The regions comprise oligopeptide sequences within amino acids 1 to 180, or within amino acids 175 to 333. The N-proximal sequence is associated with collagen activity, while the C-proximal region is associated with lectin activity.

DESCRIPTION OF SPECIFIC EMBODIMENTS

Oligopeptides are provided having substantially the same sequence as a sequence of at least about 8 amino acids coming within either the sequence 1 to 180 or 175 to 333 of conglutinin. The N-proximal sequence has collagen-like activity, while the C-terminal sequence has lectin-like activity.

Figure 2:
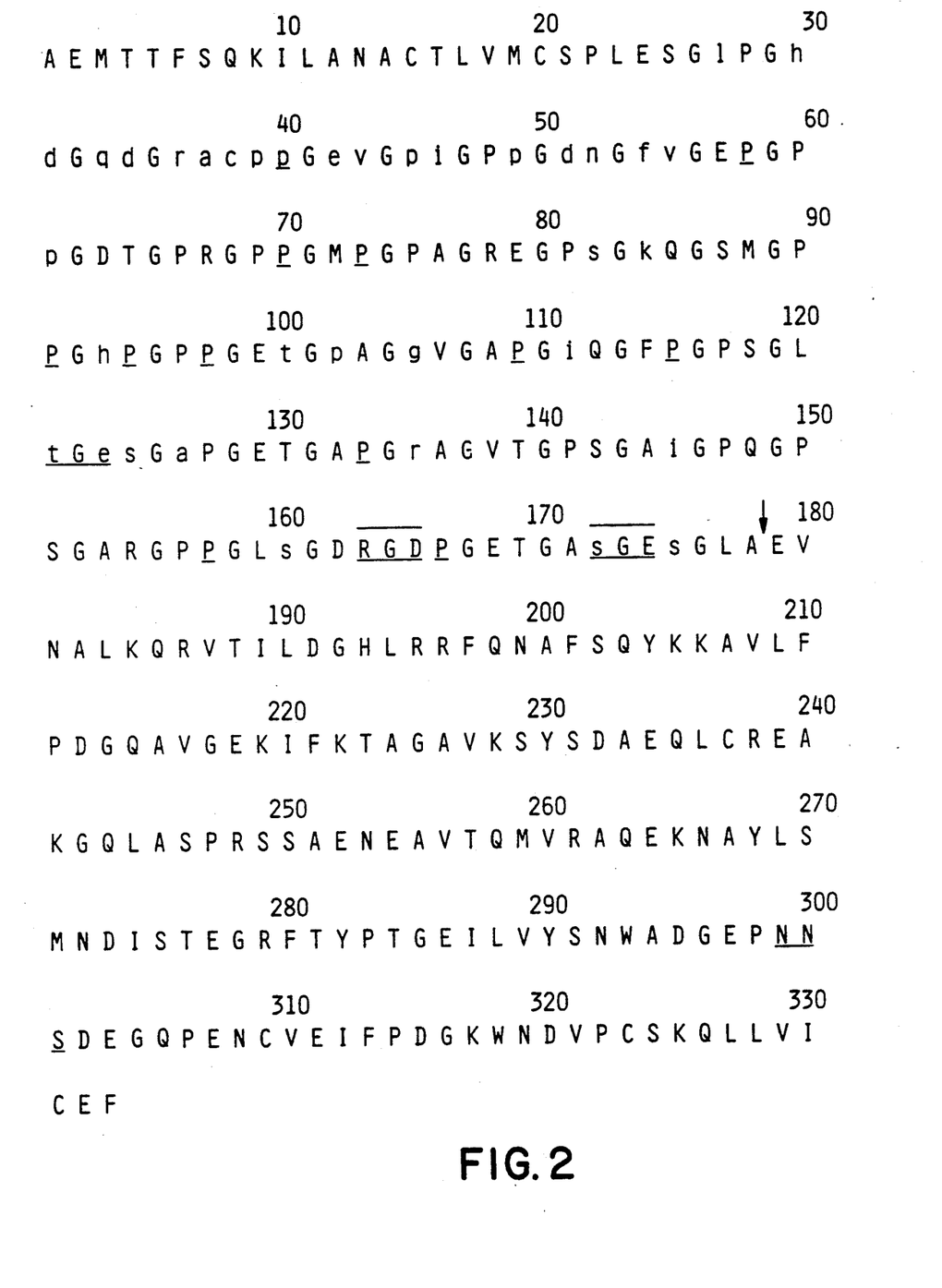
FIG. 2 shows the complete amino acid sequence of bovine conglutinin.

The oligopeptides of the subject invention will have at least 8 amino acids, usually at least about 12 amino acids, and not more than about 180 amino acids, usually not more than about 120 amino acids. The oligopeptides will have at least substantially the same sequence as a sequence found in the following sequence or the variant sequences at the site indicated as variable, usually not differing by more than 10%, more usually not differing by more than 5% of a sequence within the following sequence. The complete amino acid sequence of bovine conglutinin is also shown in FIG. 2.

```
                  10                    20                    30
       A E M T T F S Q K I L A N A C T L V M C S P L E S G l P G h 40                    50                    60
       d G q d G r a c p p G e v G p i G P p G d n G f v G E P G P 70                    80                    90
       p G D T G P R G P P G M P G P A G R E G P s G k Q G S M G P 100                   110                   120
       P G h P G P P G E t G p A G g V G A P G i Q G F P G P S G L 130                   140                   150
       t G e s G a P G E T G A P G r A G V T G P S G A i G P Q G P 160                   170                   180
       S G A R G P P G L s G D R G D P G E T G A s G E s G L A E V 190                   200                   210
       N A L K Q R V T I L D G H L R R F Q N A F S Q Y K K A V L F 220                   230                   240
       P D G Q A V G E K I F K T A G A V K S Y S D A E Q L C R E A 250                   260                   270
       K G Q L A S P R S S A E N E A V T Q M V R A Q E K N A Y L S
```

-continued

```
          280                 290                 300
M N D I S T E G R F T Y P T G E I L V Y S N W A D G E P N N
                                                        ‾ ‾
          310                 320                 330
S D E G Q P E N C V E I F P D G K W N D V P C S K Q L L V I
‾
C E F
```

In the above sequence, those sites which are not conserved among analogous proteins are shown in lower case letters, hydroxylated protein residues at the Y position of the G-X-Y motif of collagen are underlined and the carbohydrate recognition sequences at T121, S172 (O-linked) and N299 (N-linked) are also underlined. Also, the R-G-D sequence associated with the cell binding at residue numbers 163–165 is indicated by overline and underline.

In the hypervariable region, position 27 may be L or P; 30 H or S; 31 D, N, P, A or V; 33 Q, P or R; 34 D, N or A; 36 R or P; 37 E, H or A; 38 C or G; 39 P, R, S or V; 40 H, M, P or V; 42 E, P or W; 43 V or E; 45 P or L; 46 I or A; 49 S, P or Q: 51 A, D or P; 52 V, N, S or D; 54 F, R, or A; 55 V or R; 61 P or K; 82 S or M; 84 K or P; 93 H or T; 100 T, A, S, N or V; 103 P, A or I; 105 G, H or V; 111 I or R; 121 S or T; 123 A or E; 124 S or R; 126 A or D 135 H or R; 145 I or R; 160 S or T; 172 P or S; and 175 S or X.

Not only may the variable sites be substituted by each of the indicated amino acids, but in the G-X-Y motif, the X and Y positions may be substituted by proline or hydroxyproline and by conservative substitutions. The following table indicates conservative substitutions, where amino acids on the same line may be substituted one for the other.

TABLE 1

| Aliphatics |
| --- |
| Non-polar |
| G, A, P |
| I, L, V |
| Polar |
| Uncharged |
| C, S, T, M |
| N, Q |
| Charged |
| D, E |
| K, R |
| Aromatic |
| H, F, W, Y |

(N, Q, D and E may be considered as equivalent for purposes of conservative substitution).

For the N-proximal region, of particular interest is the region from about amino acid 20 to amino acid 180, more particularly the region from amino acid 25 to 60 and from 60 to 178. It is found that the region of residue 27 to 55 has hypervariability, while the region from 60 to 178 is of lesser variability. The hypervariable region has not more than 10% variation at the glycine site of the triplet, whereas the remaining sites may be widely varied. Usually, Y of the G-X-Y motif will have at least about 25%, usually at least about 50% of the amino acids as proline or hydroxyproline in the N-proximal region. The number of repeats in the oligopeptides will usually be at least about 3 and not more than about 55, generally ranging from about 4 to 51, more usually from about 6 to 40.

The N-proximal region is characterized by having from about 49 to 51 G-X-Y repeats, with 2 interruptions due to sequence variability: One is C38, where G is expected, the other is G105 at a site where an amino acid other than G is expected. 12 hydroxy-proline residues (11 of them at invariant sites) are found at position Y in the G-X-Y motif, characteristic of collagen-like molecules. The sequence has at least 3 potential carbohydrate recognition sites, of which 2 are in the variable collagen-like domain (O-linked) and 1 in the C-proximal region (N-linked). In addition, the N-proximal region includes R-G-D, a common recognition sequence for the integrin superfamily of receptors found on the surface of a variety of cells.

The conglutinin has similarity to complement protein Clq, the mannose-binding proteins (MBP) and pulmonary surfactant associated protein (PSAP) at the level of overall molecular organization. The C-proximal region, particularly residues 232–333, have significant homology with the carbohydrate recognition domain of MBP and PSAP.

The sequence homology of conglutinin extends to membrane bound animal lectins of chicken and rat hepatocytes, human asialoglycoprotein receptors, human lymphocyte Fc epsilon receptors, a matrix protein of rat cartilage proteoglycan, a soluble lectin of *Sarcophaga peregrina* humoral, lectin domains of a mouse lymph node homing receptor and of a human endothelial leukocyte adhesion molecule (ELAM-1). The conserved sites in all 15 proteins aligned includes 4 cysteines at 237, 309, 323 and 331, P298, E307, N319, W293 and W318 in the conglutinin sequence. Regions of potential functional importance, such as carbohydrate binding sites and/or divalent cation coordination appear conserved.

Depending upon the size of the subject peptides, the peptides may be prepared in a variety of ways. For amino acid sequences of less than about 60 amino acids, the peptides may be synthesized using automatic synthesizers commercially available today, for example, the ABI 430A Peptide Synthesizer. For amino acid sequences greater than about 25 amino acids, recombinant DNA technology may be employed. The sequences encoding the subject peptides may be synthetically prepared, isolated from the naturally occurring gene, may be obtained as fragments of the genomic gene or cDNA, or combinations thereof. In addition, for secretion, the sequence may be joined at its 5'-terminus of the coding strand with a sequence encoding a signal sequence which allows for secretion of the product into the supernatant. A large number of expression vectors have been described in the literature and are available or may be readily prepared. Expression cassettes are available for prokaryotes and eukaryotes. Where processing of the subject peptide is desired, such as glycosylation, eukaryotic vectors will normally be employed, using insect, fungal or mammalian hosts and vectors functional in such hosts for processing to provide for polysaccharide side chains associated with eukaryotic processing.

The subject compositions may find application in a variety of ways. The fragments from the C-proximal region may be used to inhibit binding of sugars to lectins, or may be used to bind to various sugars, to isolate molecules having the appropriate carbohydrate structure, to purify such molecules, and the like. The molecules may be by themselves, may be parts of polysomes, or associated with cells. The subject compositions may also be used for characterization, indicating the presence of the complementary carbohydrate ligand. The N-proximal sequence may find use in binding to the integrin superfamily of receptors, so as to be able to bind to cells having these receptors. In addition, the hypervariable region may serve as a molecular recognition site for binding to cells, identifying cells which bind to the hypervariable region analogous to Clq with peripheral blood mononuclear cells (Reid, *Biochem. Soc. Trans.* 11:1-12 (1983)) and collagens with chondrocytes (Mollenhauer and Von Der Mark, *EMBO J.* 2:45–50, (1983); and Mollenhauer et al., *J. Cell. Biol.* 98:1572–1578 (1984)).

The subject compounds may also be used to activate cells having surface membrane receptors to which the compounds bind. By adding a subject compound to a cell containing medium in an amount sufficient to provide for cellular activation, e.g., 1 to 100 mg/ml, cells may be activated, including proliferation and expression of proteins associated with the activated state.

The following examples are offered by way of illustration and not by way of limitation.

EXPERIMENTAL

Sequence Determination

Figure 1A:
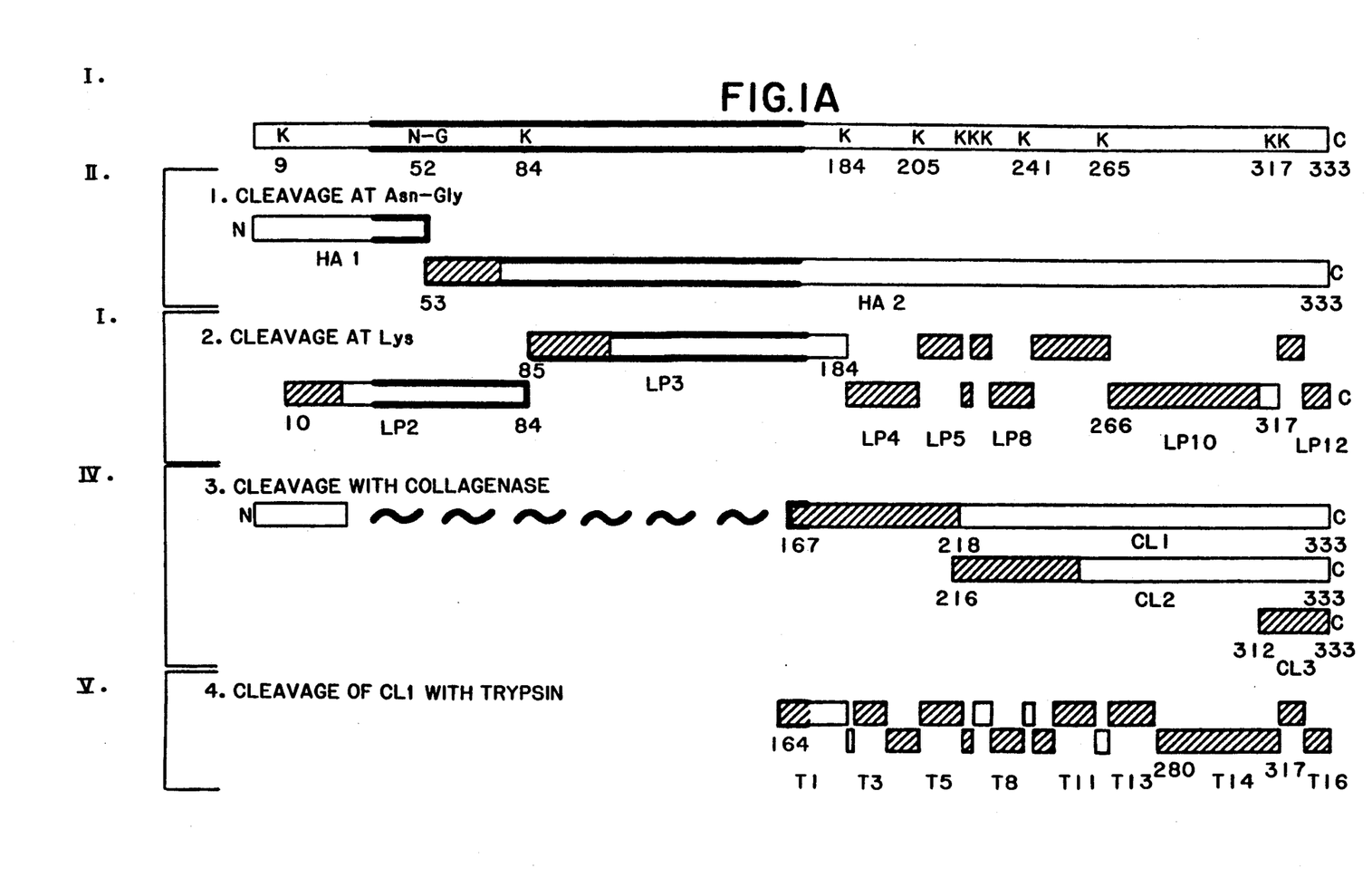
FIG. 1A describes tryptic peptides, and peptides derived by lysine specific endo-peptidase, and collagenase digestions, and FIG. 1B describes chemically cleaved peptides and subdigestion of long peptide fragments with chymotrypsin or thermolysin.

Conglutinin was isolated from individually drawn bovine blood from a local abattoir. Yeast cell wall treated protein (Strang et al., (1986) supra) was further purified on Sephacryl 400. The homogeneity of the purified protein was substantiated by SDS-PAGE and a single band of 43K was observed. Sequence information for the non-collagenous COOH-region generated by brief digestion of conglutinin by bacterial collagenase was obtained by characterization of the tryptic peptides (T in FIG. 1A-V) and of fragments CL2 and CL3 produced by prolonged collagenase digestion (FIG. 1A-IV). Sequence analysis of the COOH-region (CL1) was completed by characterization of overlapping peptides generated by lysine specific endopeptidase treatment of the intact conglutinin (LP in FIG. 1A-III).

Isolation of COOH— Terminal Domain of Conglutinin

Unmodified conglutinin was digested briefly with bacterial collagenase (25 units of collagenase per mg of conglutinin) in 25 mM Tris-HCl, 10 mM $CaCl^2$, pH 7.4 for 15 to 30 minutes at 37°. Peptides generated were purified by HPLC using a reverse phase C4 column. The isolated COOH— terminal peptide was modified with 4-vinyl pyridine before the $NH_2$— terminal amino acid sequence analysis or further fragmentation by other proteolytic enzymes.

Proteolytic Enzyme Digestion

Lysyl bonds were selectively cleaved using lysine specific endopeptidase. An enzyme to alkylated CL1 ratio (w/w) of 1:50 in 0.2M $NH_4HCO_3$, pH 8.3 for 4 hours at 37° was used. Tryptic digestion of the COOH— terminal domain was carried out similarly in 0.2M $NH_4HCO_3$ pH 7.9 at 37° for 6 hours with enzyme to substrate ratio (w/w) of 1:100.

For the collagenase domain, large peptide fragments were generated by a chemical method followed by subcleavages with proteolytic enzymes or with a second chemical. The bovine protein was treated with hydroxylamine to generate HA1 and HA2 (FIG. 1A-II). A third fragment HA3, an uncleaved protein resulting from either the highly variable site at N52 or perhaps incomplete cleavage by hydroxylamine was observed. Overlapping sequence between HA1 and HA2 was determined by characterization of peptide LP2 (FIG. 1A-III and 1B-II) obtained either from HA3 or intact conglutinin. For the same purpose, a CNBr cleaved peptide (CBx) and a o-iodosobenzoic acid peptide (IBA) was utilized, indicated in FIG. 1B-III and -IV respectively.

Figure 1B:
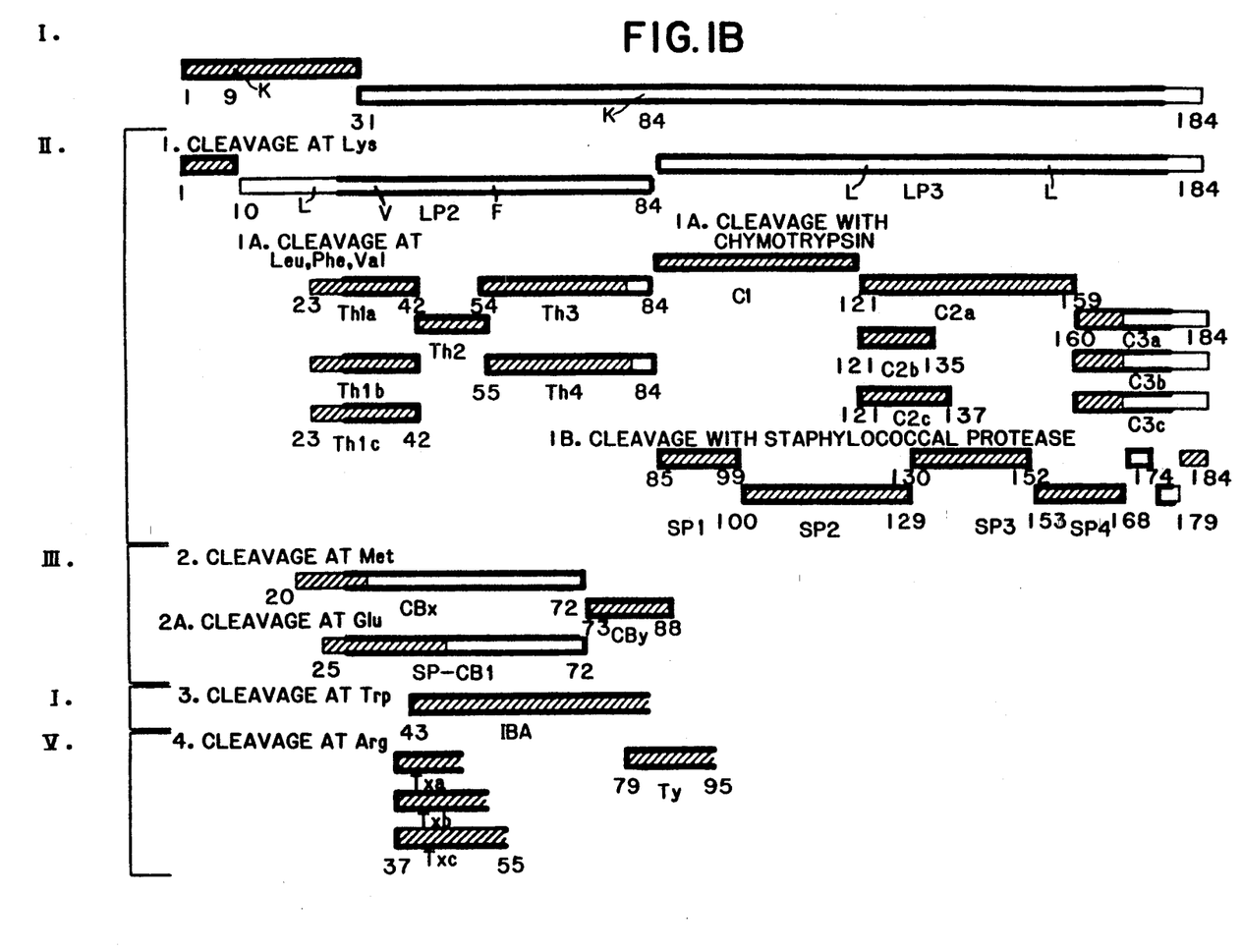

LP indicates peptides cleaved by lysine specific endopeptidase (III); CL, peptides obtained by bacterial collagenase digestion (IV). Digestion at 37° C. for 30 min. yielded CL1 (167–333). Shorter digestion (15–20 min.) generated a longer peptide, 164–333, which was used for tryptic digestion (V). Longer digestion (over 60 min.) caused breakdown of CL1 to a shorter peptide CL2. Prolonged digestion (12 h) produced CL3 as a predominant peptide. In FIG. 1B, I indicates the amino-terminal sequence analysis of intact conglutinin. Bars II, III, IV and V show the overlapping peptides used for sequencing the collagenous domain. II shows subdigestion of LP2 with thermolysin and of LP3 with chymotrypsin or *S. aureus* V8. Th denotes thermolysin peptides of LP2 originating from intact conglutinin; C, chymotrypic peptides of LP3, derived from HA3; SP, *S. aureus* V8 peptides of LP3 originating from HA3. III shows a CNBr peptide (CBx) recovered from CNBr cleavage of HA3. SP-CB1 was produced by subdigestion of CBx with *S. aureus* V8. IV shows an iodosobenzoic acid peptide (IBA) obtained by cleavage at W of the intact conglutinin. V shows 4 peptides obtained by the digestion of the protein with an arginine specific enzyme. Txa, Txb and Ty were derived from the intact conglutinin. Txc originated from HA3. Lee et al., *Arch. Biochem. Biiophys.* 241: 577–589 (1985); Mahoney and Hermondson, *Biochemistry,* 18:3810–3814 (1979).

SP-CB1 (obtained from HA3) was used initially to determine the overlapping sequence between HA1 and HA2. SP-CB1, however, did not reveal N52. Txc (originating from HA3) which has sequence homology with SP-CB1 between residues 37–54, also failed to reveal N52. The IBA obtained from intact conglutinin was subsequently analyzed. This peptide revealed sequence homology with SP-CB1 between residues 43–56 and an identical sequence with HA2 along residues 53–71. It revealed D52 and G53, but not N52. Since D52 is a deamidation product of N, which could have occurred during the chemical cleavage reaction and/or purification steps, LP2 is generated from intact conglutinin followed by subdigestion of LP2 with thermolysine. Th1a, Th1b and Th1c separated by a microbore C18 column showed sequence homology between residues 23–42 but variant sites at amino acid residues 31, 34, 37 and 40. Th1 series peptides also showed sequence homology with SP-CB1 except at residues 31, 33, 34 and 40. SP-CB1 showed multiple PTH-amino acids at certain Edman degradation cycles. Peptide Th2 aligns with peptides Txb, Txc, SP-CB1 and IBA at residues between 43–52, except at residues 49, 51 and 52. The Th2 peptide shows N52 and G53 to confirm the location of the hydroxylamine cleavage site and further verify sequence overlap between HA1 and HA2. Peptide Th3 contained an amino-terminal residue F and was sequenced through 26 cycles. The peptide showed identical sequence to the amino-terminal region of HA2. Th4 had V as the amino-terminal residue and showed sequence identity with Th3 except for K61 instead of P61. The recovery of the LP2 peptide by RP-HPLC was lower than predicted, possibly indicating that W42-containing LP2 was not recovered under the conditions used. The above results indicated a hypervariable sequence stretch existing in LP2.

Peptide LP3 also showed a variable sequence. A peptide (Ty) obtained from arginine protease treated intact conglutinin showed a sequence identical to the amino-terminal region of HA2 (residues 80–98) with the exception of M82, P84 and T93 in Ty as compared to S82, K84 and H93 in HA2. Comparison of chymotryptic peptide C1 with HA2, LP3, Ty and SP2 revealed variation of residues 93, 100, 103 and 110. Peptides C2a, C2b and C2c shared sequence homology but showed differences at residues 121, 123, 124 and 126 demonstrating hypervariability in this region. Comparison of C2 with SP3 (HA3 derived) showed a variable residue at position 135. More variable sequences were observed between C3a, C3b, C3c and SP4 (HA3 derived).

The varying sequences and the hypervariability of the N-proximal region are shown in Table 2.

TABLE 2

```
                 10            20            30            40            50            60            70            80            90
         AEMTTFSQKI LANACTLVMCS PLES GXPGXXGXXGP GXXXXGXXGXX XGXXGXXGXXG PXGXGXXGEPG PXGDTGPRGPP GMPGPAGREGP XGXQGSMGP
Th1a                               ----L---HD-QD-RECPH-E
Th1b                               ----L---HD-QD-RECPM-E
Th1c                               ----L---HN-QN-RHCPH-E
SP-CB1                             ----L---SP-PA-RAGRP-EV-PI---S-AV-FV-
                                           P  HA  Q  PECPV  PE  L      R
                                           V  R
TXa                                        AGRP-WV-PI
TXb                                        AGSP-WV-PI---P-DN
TXc                                         AGVP-WV-PI--Q-PS-AR
                                                      A
Th2                                             V-PI--P-DN
IBA                                             V-PI--S-DD-FV-----P-----------
Th3                                                         FV-----P------------------
Th4                                                          V-----K-------------------
HA2                                                         -FV-----P---------------------S-K------
C1*                                                                                          ------

C1**                                                                                         ------

C1**                                                                                         ------
C1***                                                                                        ------

C1***                                                                                        ------
Ty                                                                                       --M-P------
SP2

C2a

C2b
C2c
SP3

SP4
C3a

C3b
C3c
                100       110       120       130       140       150       160       170       180
         PGXPGPPGEXGPXGXVGAPGXQGFPGPSGLXGXXGXPGETGAPGXAGVTGPSGAXGPQGPSGARGPPGLXGQRGDPGETGAXGEXGLAEV
Th1a
Th1b
Th1c
SP—CB1

TXa
TXb
TXc

Th2
IBA
```

TABLE 2-continued

| | | | | | | | | | | |
|---|---|---|---|---|---|---|---|---|---|---|
| Th3 | --H----- | | | | | | | | | |
| Th4 | --T----- | --T--P--G----- | --I----- | | | | | | | |
| HA2 | | | H | | | | | | | |
| Cl* | --T----- | --A--A--X----- | | | | | | | | |
| | | S | | | | | | | | |
| Cl** | --T----- | --N | | | | | | | | |
| Cl*** | --H----- | --T--P--G----- | | | | | | | | |
| | | V V | | | | | | | | |
| Cl**** | --T----- | --T | | | | | | | | |
| Ty | --T----- | | | | | | | | | |
| SP2 | | T--I--G-----I----- | --X--AX--A--- | | | | | | | |
| | | R | E | | | | | | | |
| C2a | | | T--EX--A-----H----- | --I----- | | | | | | |
| | | | | R | | | | | | |
| C2b | | | S--ES--A-----R | | | | | | | |
| C2c | | | T--ER--D-----X--- | | | | | | | |
| SP3 | | | --R | --I----- | | | | | | |
| | | | | R | | | | | | |
| SP4 | | | | | -----S----- | | | | | |
| C3a | | | | | T----- | -----P--S----- | | | | |
| | | | | | s | Q | | | | |
| C3b | | | | | T----- | -----S--XX----- | | | | |
| C3c | | | | | S----- | -----X--S----- | | | | |

The subject compositions may be used in a variety of ways for identifying specific sequences associated with binding to the N-proximal region, particularly associated with a sequence of one of the hypervariable sequences of the N-proximal region of conglutinin. Thus, receptors for the different collagen-like sequences may be isolated. In addition, various carbohydrates which bind to the conserved C-proximal region of conglutinin may be isolated. Thus, the subject compositions may be used in affinity chromatography, for releasing complementary ligand binding portions from binding to conglutinin, and the like. Other uses for the subject compositions include cellular chromatography, (affinity cell separation), modulation of cellular activity, and the like. By employing the smaller fragments, one avoids having a multiplicity of functions in the same protein, so that individual characteristics may be isolated and identified.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A peptide coupled to solid support, wherein said peptide consists of a 25-153 amino acid sequence fragment from positions 181-333 of bovine conglutinin as shown in FIG. 2.

2. The peptide of claim 1 wherein said amino acid sequence includes residues 237-331 as shown in FIG. 2.

3. The peptide of claim 1 which includes positions 181-333 of FIG. 2.

* * * * *